(12) United States Patent
Gadberry et al.

(10) Patent No.: US 9,326,776 B2
(45) Date of Patent: May 3, 2016

(54) MANUALLY ACTUATED SURGICAL CLIP APPLIER

(75) Inventors: Donald L. Gadberry, San Clemente, CA (US); Frans Vandenbroek, Rancho Santa Margarita, CA (US); Gary M Johnson, Mission Viejo, CA (US); Charles C. Hart, Summerville, SC (US); David Hearn, Alta Loma, CA (US)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 1811 days.

(21) Appl. No.: 11/536,467

(22) Filed: Sep. 28, 2006

(65) Prior Publication Data
US 2007/0073314 A1     Mar. 29, 2007

Related U.S. Application Data

(60) Provisional application No. 60/721,794, filed on Sep. 29, 2005.

(51) Int. Cl.
| *A61B 17/128* | (2006.01) |
| *A61B 17/04* | (2006.01) |
| *A61B 17/00* | (2006.01) |

(52) U.S. Cl.
CPC ........... *A61B 17/128* (2013.01); *A61B 17/1285* (2013.01); *A61B 2017/0046* (2013.01); *A61B 2017/0488* (2013.01)

(58) Field of Classification Search
CPC ............... A61B 2017/0488; A61B 17/128; A61B 17/1285
USPC .......................................... 606/142, 139, 219
See application file for complete search history.

(56) References Cited

U.S. PATENT DOCUMENTS

| 3,082,426 A | 3/1963 | Miles |
| 3,363,628 A | 1/1968 | Wood |
| 3,777,538 A | 12/1973 | Weatherly et al. |
| 3,867,944 A | 2/1975 | Samuels |
| 4,152,920 A | 5/1979 | Green |
| 4,188,953 A | 2/1980 | Klieman et al. |
| 4,226,242 A | 10/1980 | Jarvik |
| 4,228,895 A | 10/1980 | Larkin |
| 4,242,902 A | 1/1981 | Green |

(Continued)

FOREIGN PATENT DOCUMENTS

| DE | 214727 | | 3/1909 |
| WO | WO/2004/008944 | * | 1/2004 |

OTHER PUBLICATIONS

Co-Pending U.S. Appl. No. 11/021,852, filed Dec. 23, 2004. Title: Surgical Instrument With Improved Handle Assembly.

(Continued)

*Primary Examiner* — Tuan V Nguyen
*Assistant Examiner* — Lucas Paez
(74) *Attorney, Agent, or Firm* — John F. Heal

(57) ABSTRACT

A surgical clip applier is provided having a cartridge carrying multiple surgical clips with a manual graspable actuator configured to sequentially deliver clips to the jaws of the clip applier. Both the cartridge and the jaws are connectable to a scissors-like handle assembly arranged to translate motion from finger loops to the jaws to open and close the jaws and thus close or crimp a delivered clip between the jaws.

20 Claims, 21 Drawing Sheets

(56) References Cited

U.S. PATENT DOCUMENTS

| | | |
|---|---|---|
| 4,246,903 A | 1/1981 | Larkin |
| 4,296,751 A | 10/1981 | Blake, III et al. |
| 4,299,224 A | 11/1981 | Noiles |
| 4,316,468 A | 2/1982 | Klieman et al. |
| 4,372,316 A | 2/1983 | Blake, III et al. |
| 4,397,312 A | 8/1983 | Molko |
| 4,408,603 A | 10/1983 | Blake, III et al. |
| 4,412,539 A | 11/1983 | Jarvik |
| 4,425,915 A | 1/1984 | Ivanov |
| 4,430,997 A | 2/1984 | DiGiovanni et al. |
| 4,452,376 A | 6/1984 | Klieman et al. |
| 4,500,024 A | 2/1985 | DeGiovanni et al. |
| 4,509,518 A | 4/1985 | McGarry et al. |
| 4,522,207 A | 6/1985 | Klieman et al. |
| 4,534,351 A | 8/1985 | Rothfuss et al. |
| 4,557,263 A | 12/1985 | Green |
| 4,572,183 A | 2/1986 | Juska |
| 4,611,595 A | 9/1986 | Klieman et al. |
| 4,616,650 A | 10/1986 | Green et al. |
| 4,624,254 A | 11/1986 | McGarry et al. |
| 4,662,374 A | 5/1987 | Blake, III |
| 4,674,504 A | 6/1987 | Klieman et al. |
| 4,702,247 A | 10/1987 | Blake, III et al. |
| 4,712,549 A | 12/1987 | Peters et al. |
| 4,799,481 A | 1/1989 | Transue et al. |
| 4,844,066 A | 7/1989 | Stein |
| 4,850,355 A | 7/1989 | Brooks et al. |
| 4,971,198 A | 11/1990 | Mericle |
| 4,976,722 A | 12/1990 | Failla |
| 4,979,950 A | 12/1990 | Transue et al. |
| 5,030,226 A | 7/1991 | Green et al. |
| 5,047,038 A | 9/1991 | Peters et al. |
| 5,049,152 A | 9/1991 | Simon et al. |
| 5,084,057 A | 1/1992 | Green et al. |
| 5,104,395 A | 4/1992 | Thornton et al. |
| 5,112,343 A | 5/1992 | Thornton |
| 5,201,746 A | 4/1993 | Shichman |
| 5,222,961 A * | 6/1993 | Nakao et al. ............ 606/143 |
| 5,246,450 A | 9/1993 | Thornton et al. |
| 5,300,081 A | 4/1994 | Young et al. |
| 5,354,304 A | 10/1994 | Allen et al. |
| 5,366,134 A | 11/1994 | Green et al. |
| 5,431,668 A | 7/1995 | Burbank, III et al. |
| 5,497,933 A * | 3/1996 | DeFonzo et al. ............ 227/175.1 |
| 5,509,920 A | 4/1996 | Phillips et al. |
| 5,514,149 A | 5/1996 | Green et al. |
| 5,527,318 A | 6/1996 | McGarry |
| 5,527,320 A | 6/1996 | Carruthers et al. |
| 5,542,949 A | 8/1996 | Yoon |
| 5,544,802 A | 8/1996 | Crainich |
| 5,607,436 A | 3/1997 | Pratt et al. |
| 5,626,592 A | 5/1997 | Phillips et al. |
| 5,634,930 A | 6/1997 | Thornton et al. |
| 5,643,291 A | 7/1997 | Pier et al. |
| 5,700,270 A | 12/1997 | Peyser et al. |
| 5,713,911 A | 2/1998 | Racenet et al. |
| 5,769,857 A | 6/1998 | Reztzov et al. |
| 5,772,673 A | 6/1998 | Cuny et al. |
| 5,833,696 A | 11/1998 | Whitfield et al. |
| 5,843,097 A | 12/1998 | Mayenberger et al. |
| 5,868,759 A | 2/1999 | Peyser et al. |
| 5,868,761 A | 2/1999 | Nicholas et al. |
| 5,893,875 A * | 4/1999 | O'Connor et al. ............ 606/205 |
| 5,895,394 A | 4/1999 | Kienzle et al. |
| 5,904,693 A | 5/1999 | Dicesare et al. |
| 5,938,667 A | 8/1999 | Peyser et al. |
| 6,059,799 A | 5/2000 | Aranyi et al. |
| 6,179,850 B1 | 1/2001 | Goradia |
| 6,306,149 B1 | 10/2001 | Meade |
| 6,306,150 B1 | 10/2001 | Levinson |
| 6,352,541 B1 | 3/2002 | Kienzle et al. |
| 6,423,079 B1 | 7/2002 | Blake, III |
| 6,446,854 B1 | 9/2002 | Remiszewski et al. |
| 6,520,972 B2 | 2/2003 | Peters |
| 6,599,298 B1 | 7/2003 | Forster et al. |
| 6,610,073 B1 | 8/2003 | Levinson |
| 6,610,074 B2 | 8/2003 | Santilli |
| RE38,445 E | 2/2004 | Pistl et al. |
| 6,824,547 B2 | 11/2004 | Wilson, Jr. et al. |
| 6,837,895 B2 | 1/2005 | Mayenberger |
| 6,840,945 B2 | 1/2005 | Manetakis et al. |
| 6,849,079 B1 | 2/2005 | Blake, III et al. |
| 6,896,683 B1 | 5/2005 | Gadberry et al. |
| 7,052,504 B2 | 5/2006 | Hughett |
| 2002/0099388 A1 | 7/2002 | Mayenberger |
| 2002/0177863 A1 | 11/2002 | Mandel et al. |
| 2003/0225423 A1 | 12/2003 | Huitema |
| 2004/0010272 A1 | 1/2004 | Manetakis et al. |
| 2004/0097970 A1 | 5/2004 | Hughett |
| 2004/0138681 A1 | 7/2004 | Pier |
| 2004/0153100 A1 * | 8/2004 | Ahlberg et al. ............ 606/140 |
| 2005/0065537 A1 | 3/2005 | Tangherlini et al. |
| 2005/0085830 A1 | 4/2005 | Lehman et al. |
| 2005/0113847 A1 | 5/2005 | Gadberry et al. |
| 2005/0177177 A1 | 8/2005 | Viola |
| 2005/0222588 A1 | 10/2005 | Vandenbroek et al. |
| 2005/0234478 A1 * | 10/2005 | Wixey et al. ............ 606/142 |
| 2005/0256529 A1 | 11/2005 | Yawata et al. |
| 2005/0273122 A1 | 12/2005 | Theroux et al. |
| 2006/0047305 A1 | 3/2006 | Ortiz et al. |
| 2006/0047306 A1 | 3/2006 | Ortiz et al. |
| 2006/0079913 A1 | 4/2006 | Whitfield et al. |
| 2006/0161182 A1 | 7/2006 | Vandenbroek |
| 2007/0093856 A1 * | 4/2007 | Whitfield et al. ............ 606/142 |
| 2008/0140090 A1 * | 6/2008 | Aranyi et al. ............ 606/143 |

OTHER PUBLICATIONS

Co-Pending U.S. Appl. No. 10/381,970, filed Mar. 5, 2004, Title: Multiple Clip Applier Apparatus and Method.

Co-Pending U.S. Appl. No. 11/039,188, filed Jan. 19, 2005. Title: Single Fire Vascular Clip Applier With Disposable Jaw.

Co-Pending U.S. Appl. No. 10/518,436, filed Dec. 16, 2004. Title: Clip Applier Cartridge With Internal Ratchet.

Co-Pending U.S. Appl. No. 10/815,149, filed Mar. 30, 2004. Title: Convertible Surgical Clip Applier System.

European Patent Office, International Search Report and the Written Opinion of the International Searching Authority for PCT Application No. PCT/US2006/037596, mailed Feb. 22, 2007.

The International Bureau of WIPO, International Preliminary Report on Patentability for International Application No. PCT/US2006/037596, mailed Apr. 10, 2008.

* cited by examiner

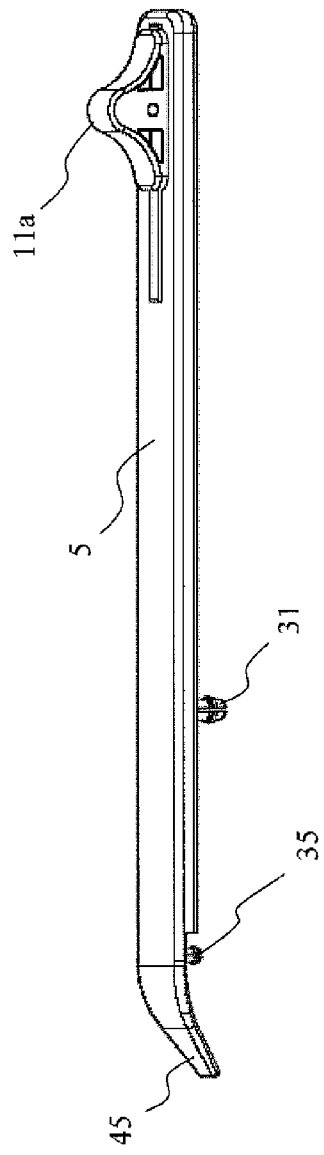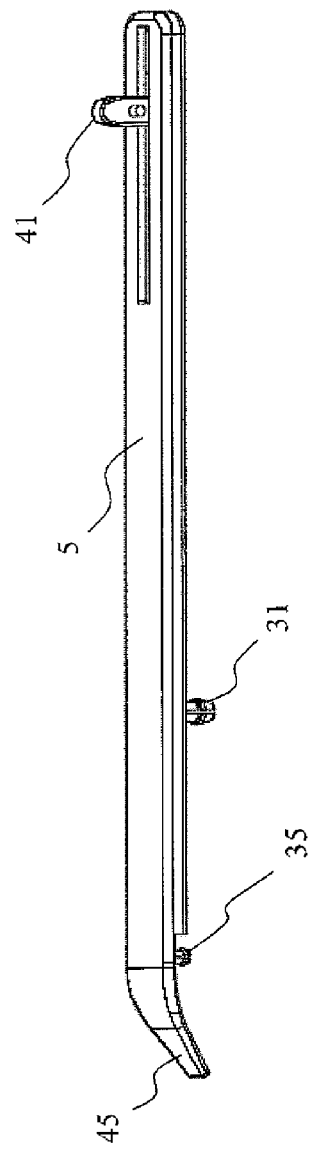
FIG. 5A
FIG. 5B

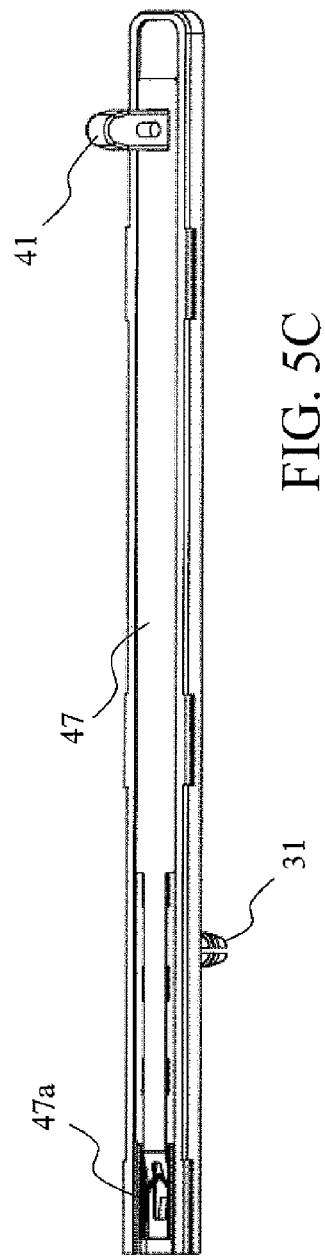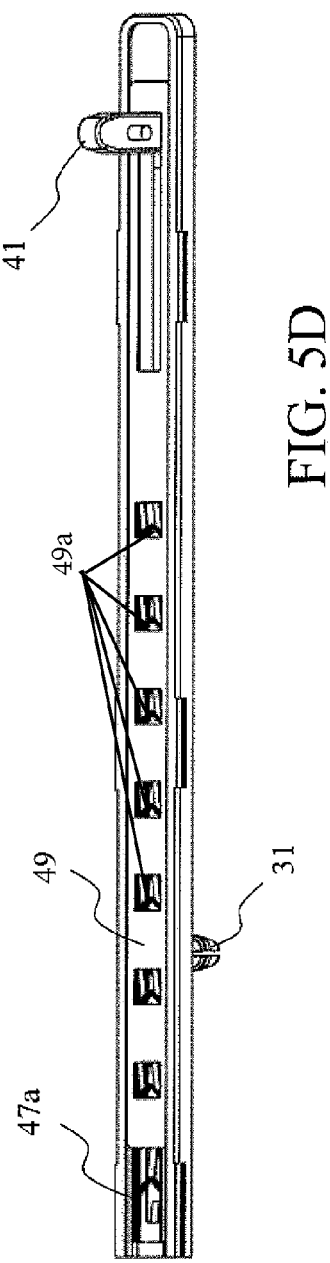

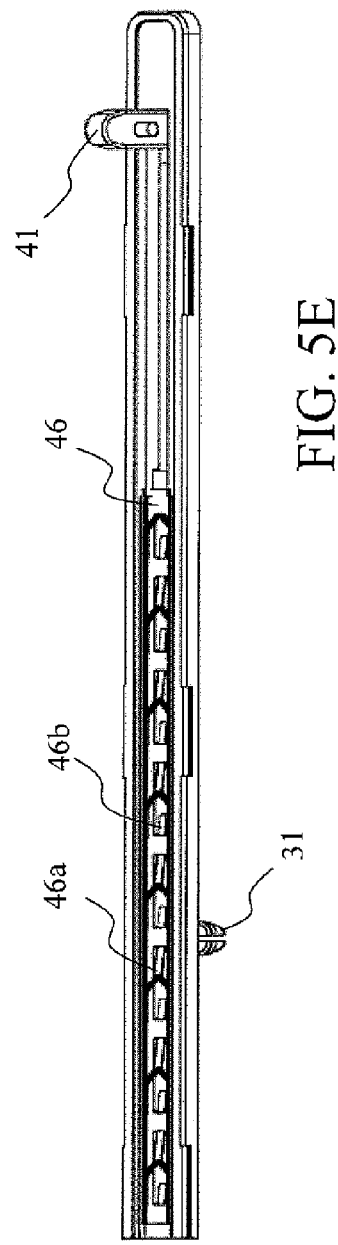
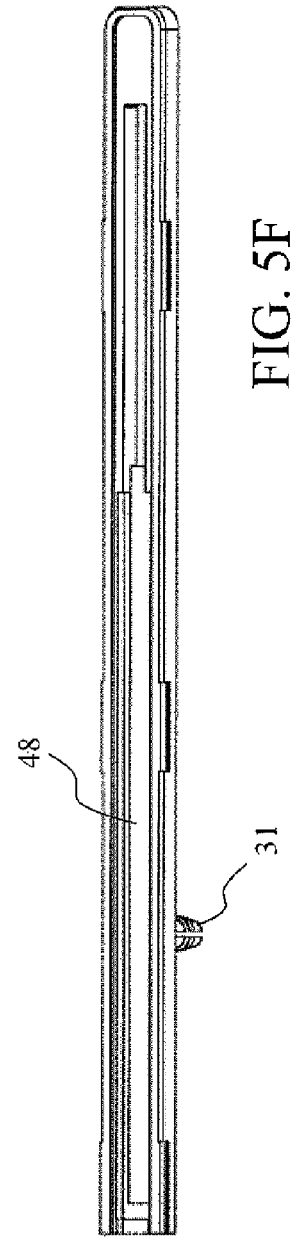
FIG. 5E
FIG. 5F

MANUALLY ACTUATED SURGICAL CLIP APPLIER

CROSS-REFERENCE TO RELATED APPLICATIONS

This application claims the benefit of U.S. Provisional Application No. 60/721,174, filed Sep. 29, 2005, the disclosure of which is hereby incorporated by reference as if set forth in full herein.

BACKGROUND

This invention relates generally to surgical clip appliers and more specifically to manually actuated clip appliers.

Surgical clips are commonly used to occlude body conduits such as blood vessels. For example, clip appliers have been used to place a clip in an open state over the blood vessel and crimp the clip to a closed state to pinch and hold the vessel in an occluded configuration.

In some cases, the clip appliers are adapted to work with only one clip at a time. The jaws of the clip applier are used to grab a clip from a plurality of clips separated and evenly distributed on a clip rack. The clip is then placed and crimped onto the blood vessel. To place another clip onto the blood vessel, the clip applier is used again to grab a clip from the clip rack using the clip applier's jaws. This process can be tedious, time consuming and difficult, as the clips are quite small. Such clip appliers are commonly referred to as single-fire clip appliers.

By comparison, multiple-fire clip appliers have multiple clips housed in a clip cartridge, which is connected to a handle and trigger assembly. Operation of the trigger causes one of the clips in the cartridge to be automatically loaded into the jaws for ultimate application at the operative site. With such a device, multiple clips can be quickly applied at the site by successive operation of the trigger. However, such clip appliers are often complex requiring numerous components and timing mechanisms and thereby reducing reliability and increasing cost. Also, being automatic and the operational trigger being largely divorced from the application of force to the clip, such appliers often do not offer the tactical feedback to provide a surgeon some indication as to the amount of force being applied by the clip to the body tissue, such as a blood vessel.

Single-fire and multi-fire clip appliers can also be reusable to reduce costs. Reusable clip appliers are sometimes formed of metal and are designed for repeated use and sterilization, for example, in an autoclave. It is this autoclaving procedure, which can result in the bending or otherwise damaging of the jaws, as well as disrupting clip alignment mechanisms and the clip applier's general ability to receive and apply the clip.

SUMMARY

In accordance with various aspects of the present invention, a surgical clip applier comprises a handle assembly having two movable handles, jaws connected to the handle assembly, a cartridge carrying multiple surgical clips connected to the handle assembly. The cartridge has a manually movable actuator attached to the cartridge arranged to operationally advance at least one of the multiple surgical clips.

In one aspect, a surgical clip applier comprises a cartridge having a proximal end and a distal end, a connector arranged to extend from the distal end of the cartridge and jaws connected to the proximal end of the cartridge. A release tab extends from the distal end of the cartridge. The clip applier also comprises a handle assembly that has a proximal end and a distal end. The cartridge is removably connected to the proximal and distal ends of the handle assembly, the distal end of the handle assembly having a plurality of slots arranged to receive the connector.

In one aspect, a surgical clip applier comprises a cartridge carrying multiple surgical clips having a first connector and a second connector, and a longitudinal axis extending from a distal end of the cartridge to a proximal end of the cartridge. Each clip is U-shaped with first and second legs. The clip applier also comprises a first jaw having a slot and arranged to receive one of the first and second legs of one clip of the multiple surgical clips, the first jaw having an aperture extending through the first jaw in a direction orthogonal to the longitudinal axis. The first connector is operationally connected to the aperture of the first jaw. The clip applier also comprises a second jaw having a slot and arranged to receive one of the first and second legs of one clip of the multiple surgical dips. A plate connects the first and second jaws together and has an aperture through the plate. The second connector is operationally connected to the aperture through the plate and a handle assembly is removably connected to the cartridge and the plate.

Many of the attendant features of the present invention will be more readily appreciated as the same becomes better understood by reference to the foregoing and following description and considered in connection with the accompanying drawings in which like reference symbols designate like parts throughout.

BRIEF DESCRIPTION OF THE DRAWINGS

FIG. 5A illustrates a perspective view of one aspect of a cartridge in accordance with various aspects of the present invention;

FIGS. 5B-F illustrate perspective views of aspects of a cartridge in accordance with various aspects of the present invention with the cartridge partially disassembled;

DETAILED DESCRIPTION

In this description, "proximal" or "proximally" refers to that portion of the instrument, component, or element that extends toward the user. "Distal" or "distally" refers to that portion of the instrument, component, or element that extends away from the user. In accordance with various aspects of the present invention, a surgical clip applier system is provided with a cartridge carrying multiple surgical clips, jaws and a handle assembly. In one aspect, a new cartridge may offer a new set of jaws with a new set of clips. In one aspect, the jaws, cartridge and handle assembly are separately connectable allowing one set of jaws and handle assembly to be used in a single procedure with multiple cartridges. In one aspect, the cartridge can be reloaded with additional clips without replacing the entire cartridge.

Figure 1A:
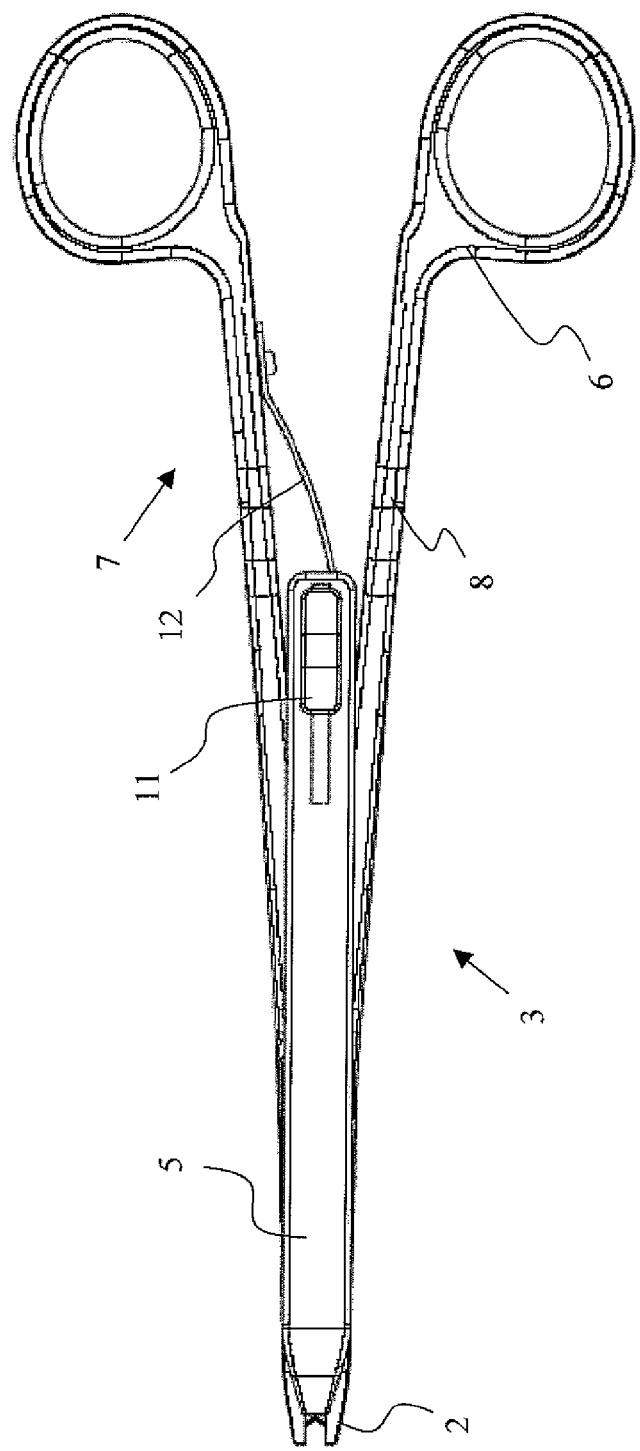
FIG. 1A illustrates a top view of one aspect of a surgical clip applier in accordance with various aspects of the present invention.
Figure 1B:
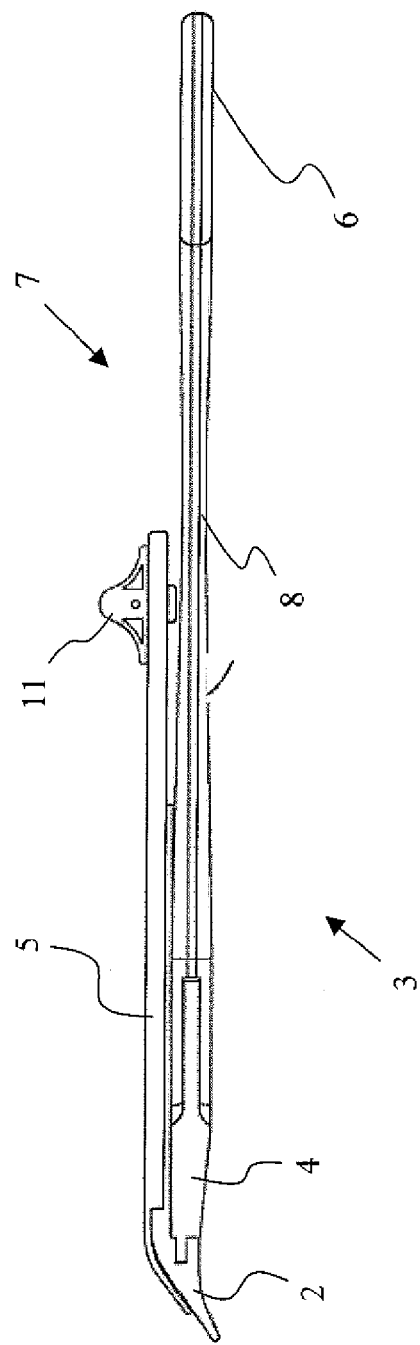
FIG. 1B illustrates a side view of one aspect of a surgical clip applier in accordance with various aspects of the present invention.
Figure 1C:
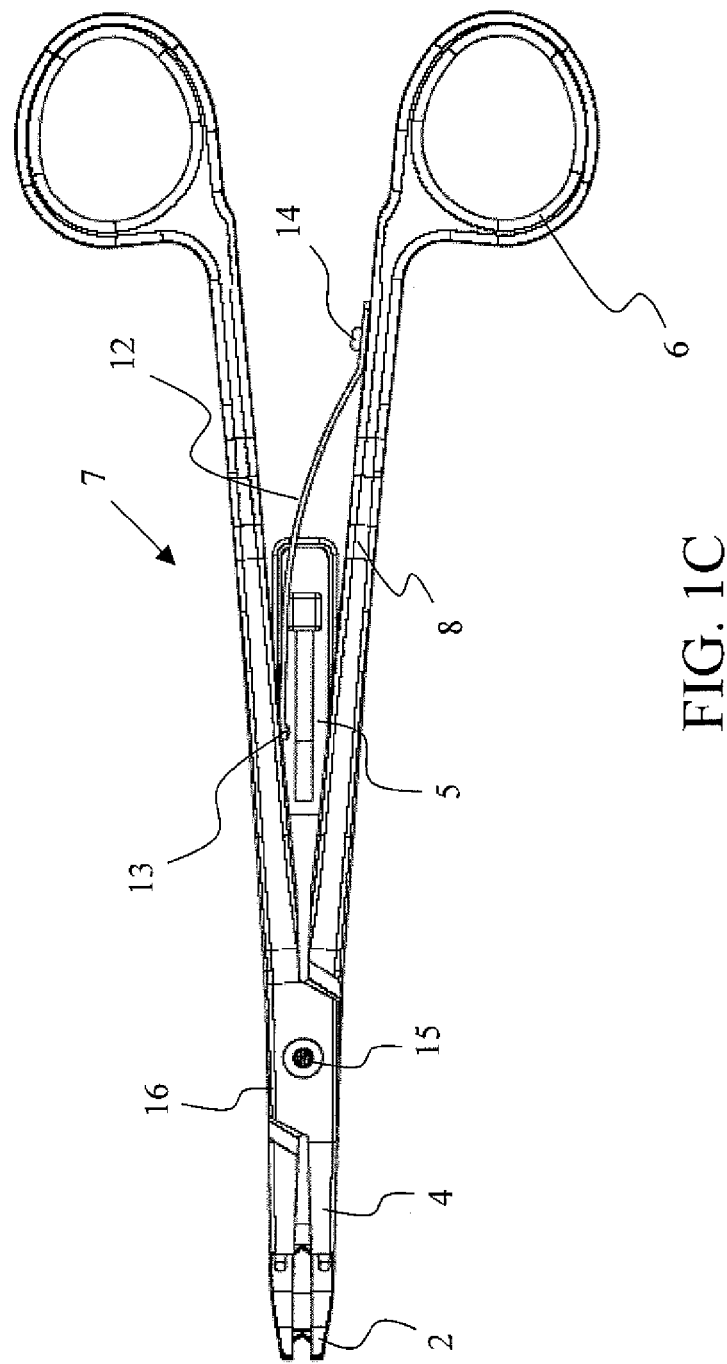
FIG. 1C illustrates a bottom view of one aspect of a surgical clip applier in accordance with various aspects of the present invention.
Figure 1D:
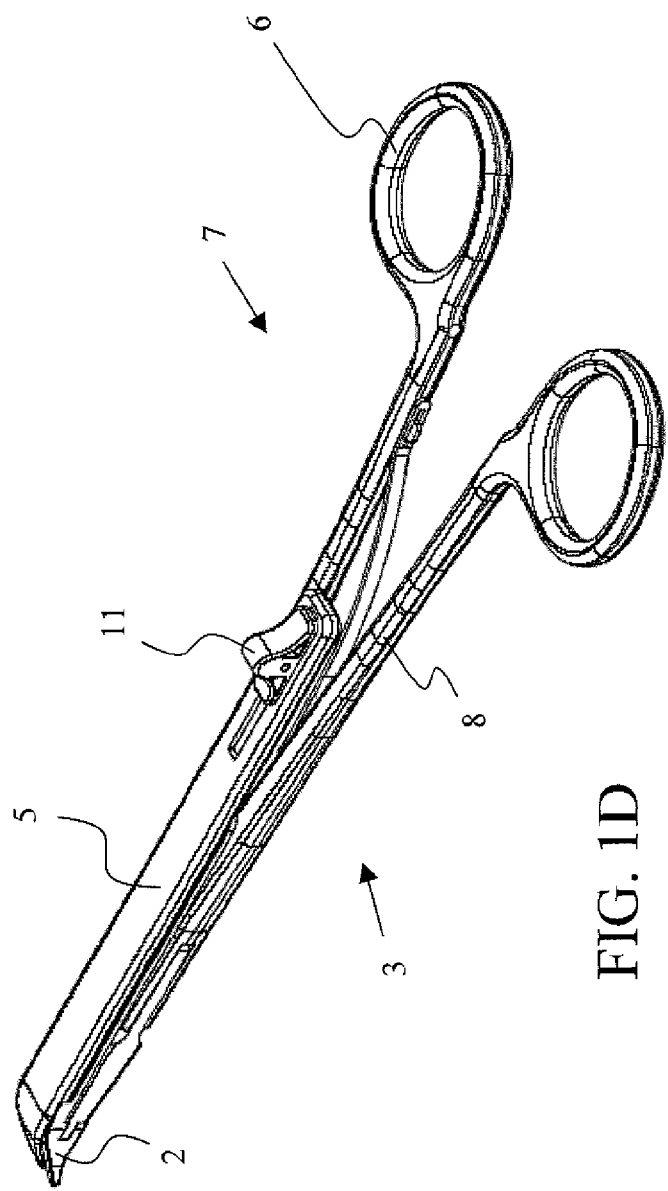
FIG. 1D illustrates a perspective view of one aspect of a surgical clip applier in accordance with various aspects of the present invention.
Figure 2:
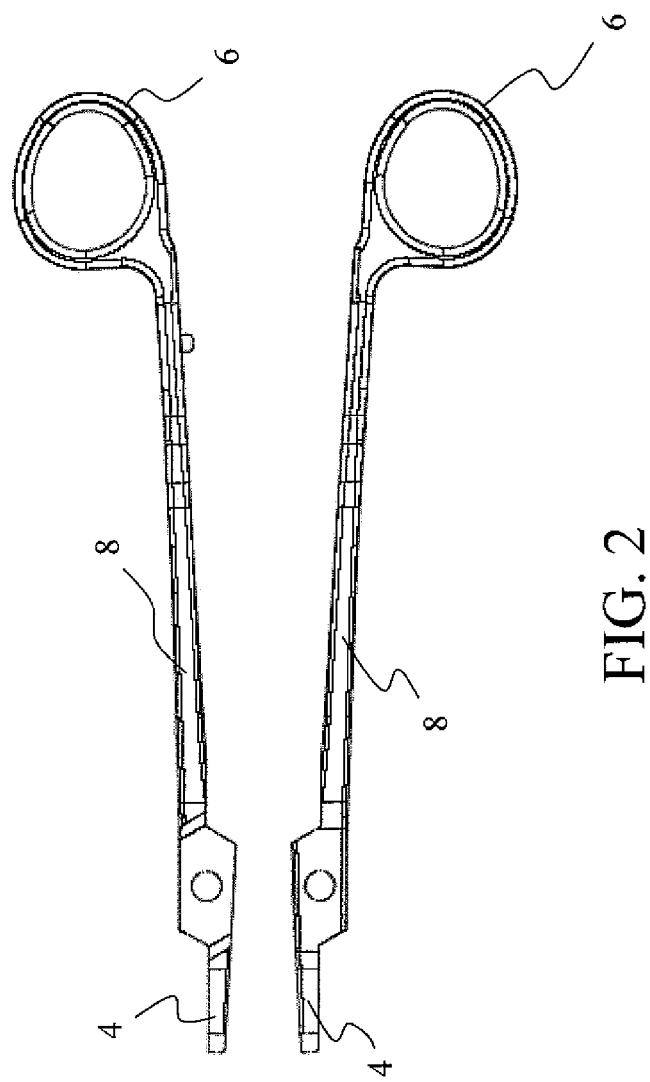
FIG. 2 illustrates a top view of one aspect of a handle assembly disassembled in accordance with various aspects of the present invention.
Figure 3A:
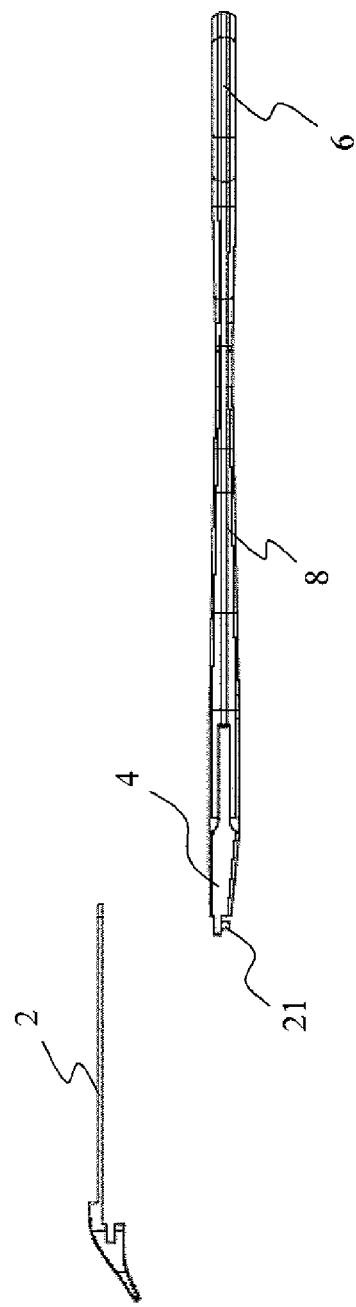
FIG. 3A illustrates a side view of one aspect of a surgical clip applier in accordance with various aspects of the present invention with jaws separated from the surgical clip applier.
Figure 3B:
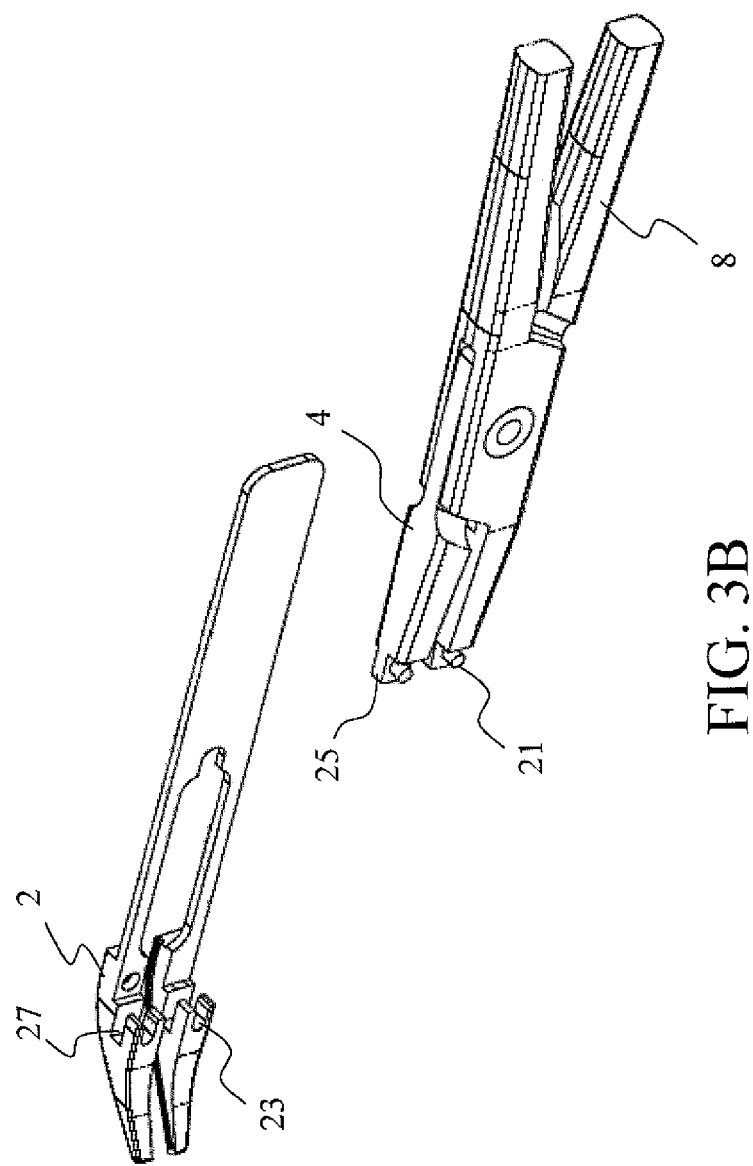
FIG. 3B illustrates a close-up view of one aspect of a surgical clip applier in accordance with various aspects of the present invention with jaws separated from the surgical clip applier.
Figure 3C:
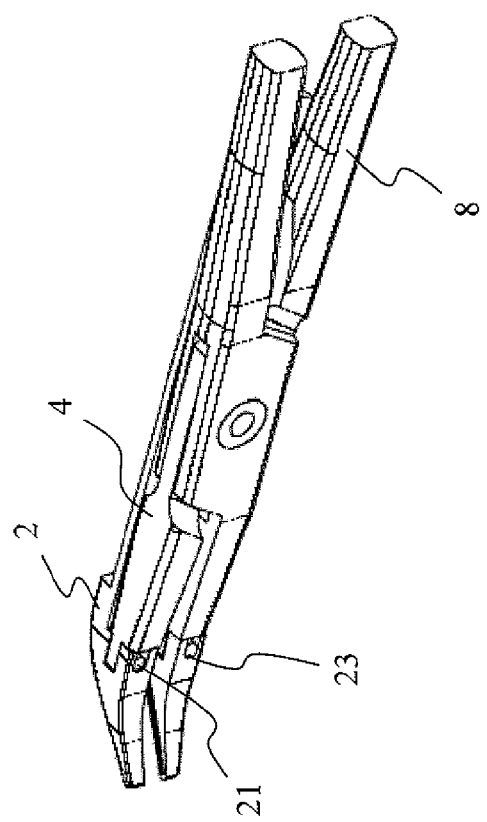
FIG. 3C illustrates a close-up view of one aspect of a surgical clip applier in accordance with various aspects of the present invention with jaws coupled to the surgical clip applier.
Figure 4A:
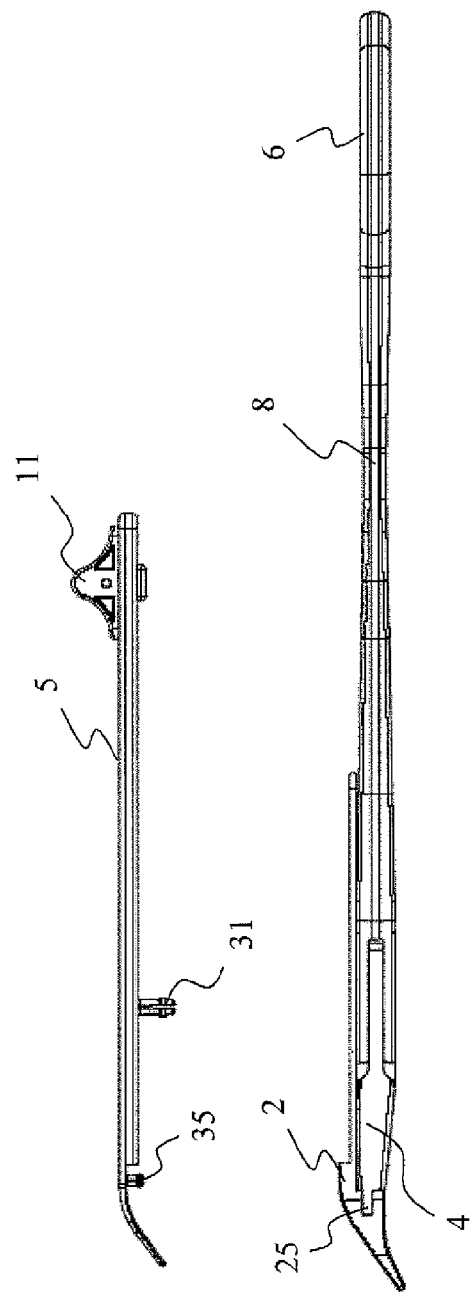
FIG. 4A illustrates a side view of one aspect of a surgical clip applier in accordance with various aspects of the present invention with a cartridge separated from the surgical clip applier.
Figure 4B:
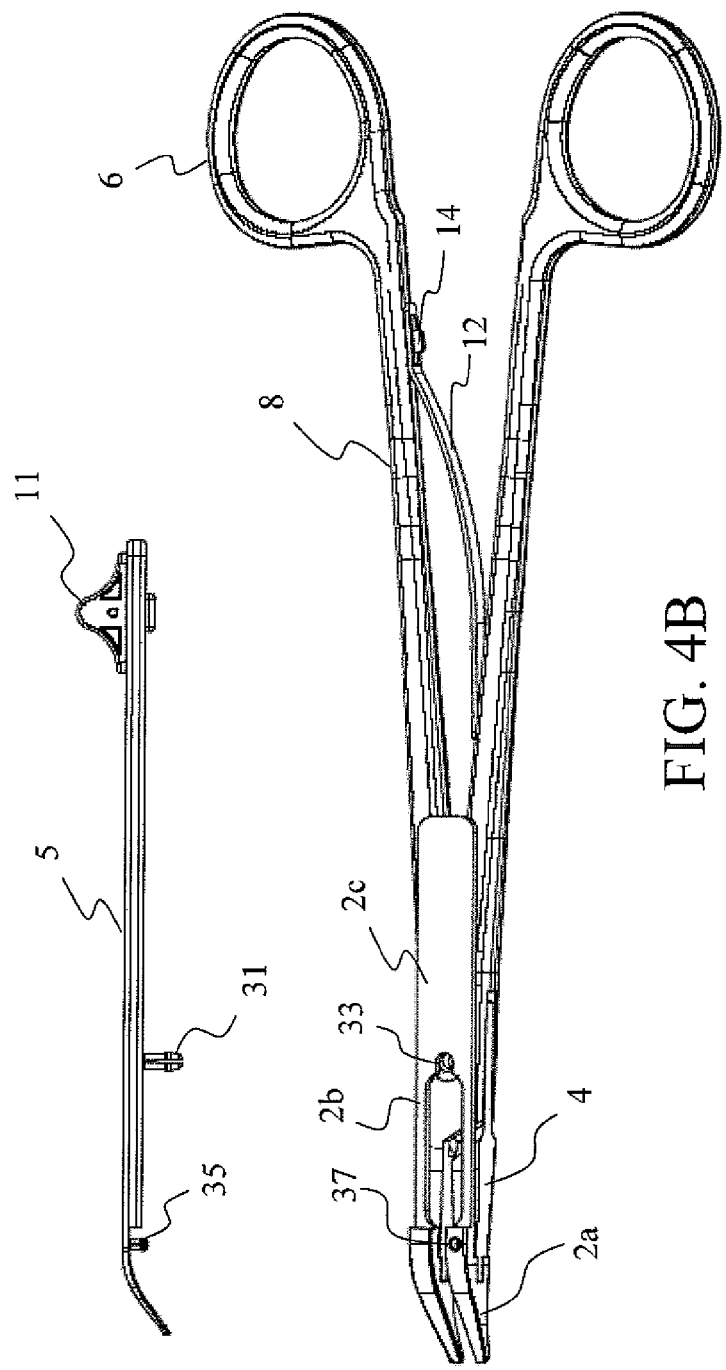
FIG. 4B illustrates a perspective view of one aspect of a surgical clip applier in accordance with various aspects of the present invention with a cartridge separated from the surgical clip applier.
Figure 6A:
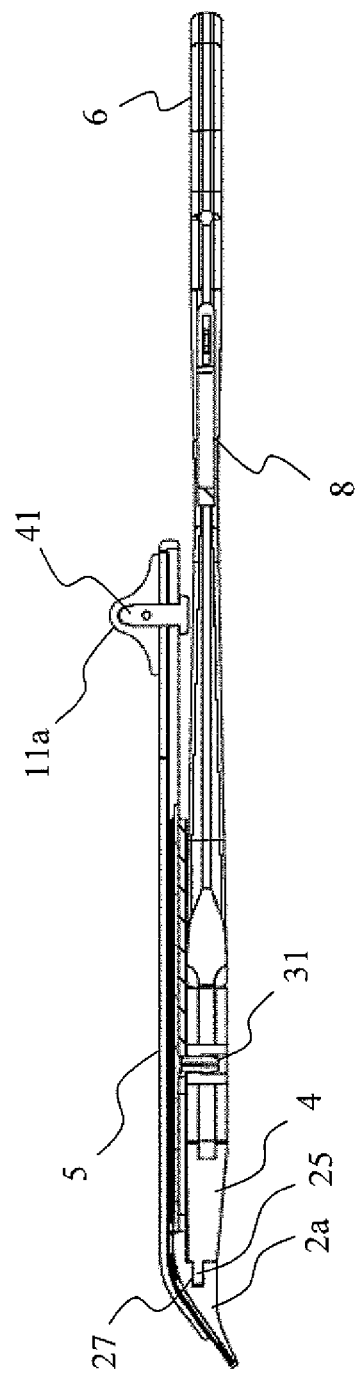
FIGS. 6A-B illustrate cross-sectional side views of one aspect of a surgical clip applier in accordance with various aspects of the present invention.
Figure 6B:
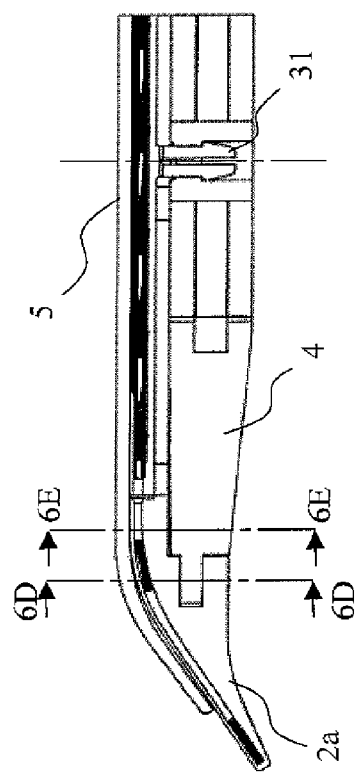
Figure 6C:
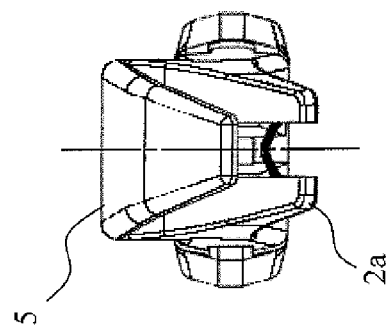
FIG. 6C illustrates a front view of one aspect of a surgical clip applier in accordance with various aspects of the present invention.
Figure 6D:
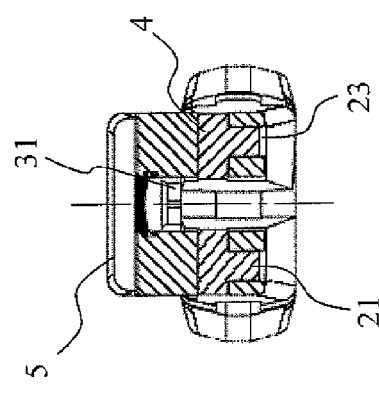
FIG. 6D illustrates cross-sectional view taken along section lines 6D-6D of FIG. 6B in accordance with various aspects of the present invention.
Figure 6E:
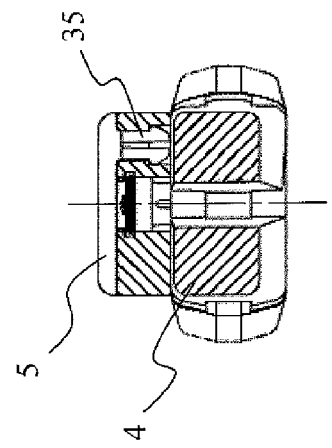
FIG. 6E illustrates cross-sectional view taken along section lines 6E-6E of FIG. 6B in accordance with various aspects of the present invention.
Figure 7B:
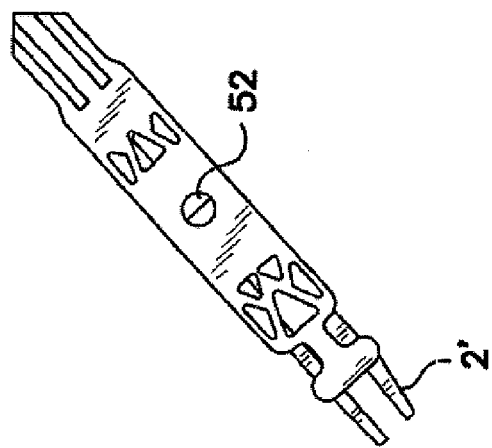
FIGS. 7A-B illustrate close up perspective views of one aspect of a surgical clip applier in accordance with various aspects of the present invention without a cartridge.
Figure 7A:
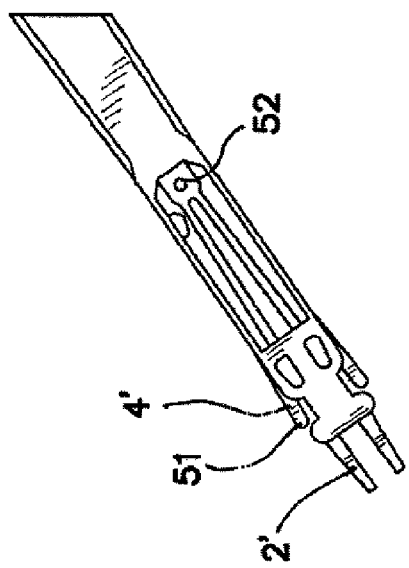
Figure 7C:
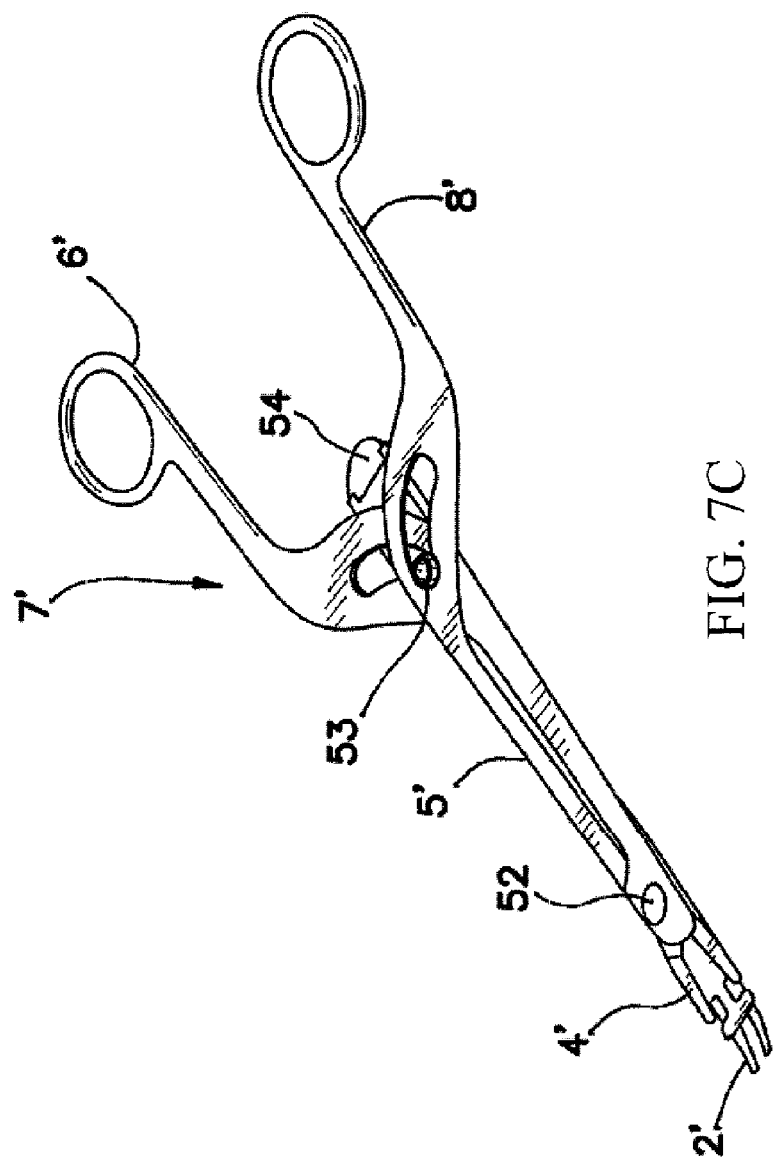
FIG. 7C illustrates a perspective view of one aspect of a surgical clip applier in accordance with various aspects of the present invention.
Figure 7E:
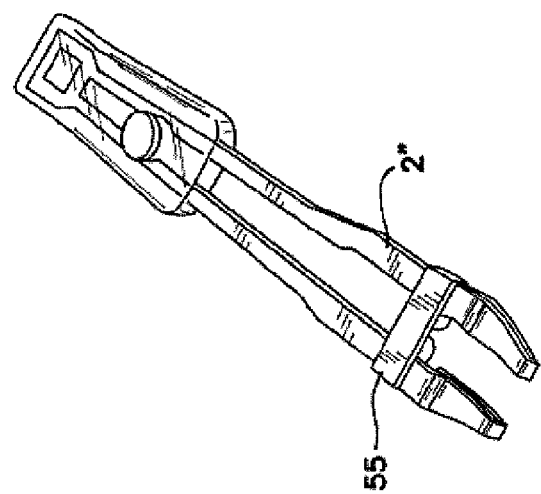
FIG. 7E illustrate close up perspective view of one aspect of jaws of a surgical clip applier in accordance with various aspects of the present invention.
Figure 7D:
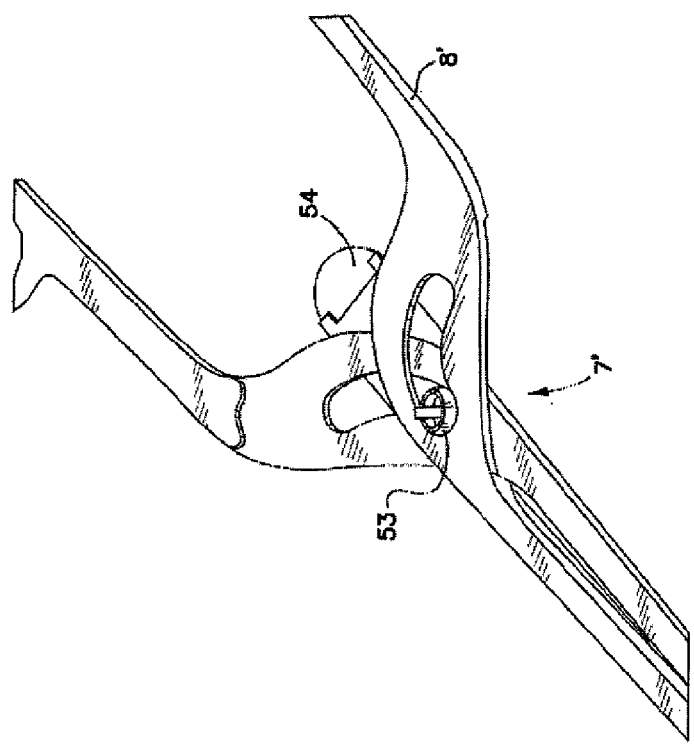
FIG. 7D illustrates close up perspective view of one aspect of a surgical clip applier in accordance with various aspects of the present invention.

Referring to FIGS. 1-3, a clip applier 3 is shown according to various aspects of the present invention. The dip applier has a cartridge 5 and a handle assembly 7. The cartridge 5 is coupled to the handle assembly 7 in a snap-type fit relation in which a post extending from the cartridge snaps or latches into an opening or aperture disposed in the handle assembly. The handle assembly resembles a scissors configuration having a pair of intersecting handles 8 crossing at a pivot point with finger loops 6 at one end of each handle and end effectors 4 at the other end of each handle.

The cartridge 5 is coupled to jaws 2 in which a clip from the cartridge is fed and ultimately crimped or closed on the operative site, tissue or object. One or more clips are housed in the cartridge 5 and are fed one at a time to the jaws 2. An actuator 11 positioned on the cartridge controls the placement of the clip into the jaws in response to manipulation of the actuator by a surgeon's thumb or fingers. In one aspect, the actuator 11 is a slider knob having converging tapered sides configured for comfortable placement and gripping by a surgeon's thumb and/or fingers. For example, a user is able to push it forward and back with an index finger while holding the handles with the thumb and remaining fingers. Sliding the actuator 11 in a first direction, e.g., distally, a clip from the cartridge 5 is moved into the jaws 2. Successive or remaining clips in the cartridge also move towards the jaws. The actuator 11 is slid back in a second or reverse direction, e.g., proximally, to retrieve the next clip to be applied and crimped.

The end effectors 4 of the handles 8 operatively engage the jaws 2. Movement of the handles 8 together causes the jaws 2 to close or move together. With the actuation or manipulation of the handles 8 being separate from clip feeder actuation, the jaws 2 may be closed with or without a clip being between the jaws. As such, the jaws may be used separately and independently, for example, to test an operative site before placement of the clip, to grasp tissue or an object, or to clear a pathway or view of the operative site.

In one aspect, a cantilever spring 12 is coupled between the handles 8. A post 13, such as a rivet or drive screw, connects one end of the spring 12 to one of the handles 8 and a stop tab 14 holds the other end of the spring 12 to the other handle 8 providing a position stop and allowing for movement of the end of the spring through a slot in the spring itself. The post 13 is placed along a first sidewall of one handle distally or closer to the jaws than the stop tab 14 placed along a second sidewall facing the first sidewall. As such, the spring 12 spans between the handles 8. The spring is configured to bias or hold the jaw ends in a set or initial position. As such, in one aspect, the spring force, together with the jaws being of a horseshoe shaped ridged metal, are together positioned and formed to maintain a predetermined gap between the jaw ends. Thus, the gap between the jaw ends or tips is maintained as the spring and jaws in unison holds the handles in position, such that the jaws 2 do not close or open further but remain at an initial, e.g., manufactured or assembled, position.

The spring 12 also, in one aspect, biases or counteracts pressure or forces applied by someone, e.g., a surgeon, picking up or otherwise handling the clip applier by the handles. As such, in one aspect, for a clip to be crimped or the jaws to be closed, sufficient force is applied by squeezing the handles together to overcome the force or bias of the spring 12. The spring or one or both post and stop tab may also be moved, e.g., tightened or otherwise repositioned, to adjust the predetermined or set position of the jaws and handles relative to each other. In one aspect, the handles are also connected to each other through a post 15 and a lock box 16. A complementary lock box is disposed in each handle limiting over opening and closing of the handles and assisting in alignment and pivotal movement of each handle. The post extends through at least a portion of each lock box on each handle connecting the handles together in a pivot or scissors like configuration.

Referring now to FIGS. 4A-4B and 6A-6E, the jaws 2 may be separable or connectable separately to the handle assembly 7 and the cartridge 5. Each end effector 4 of each handle 8 has a projection or post 21 extending generally perpendicularly from the longitudinal axis of the clip applier or a plane generally traversed by the handles 8 during each stroke. The jaws 2 have respective receivers 23 to attach to the projections 21 of the end effectors 4. In one aspect, the receivers 23 are cavities laterally extending into the jaws 2 and generally "c-shaped" recesses or grooves. Lateral portions or planar projections 25 of the end effectors 4 slide into lateral cavities or planar slots 27 in the jaws 2. The projections 21 extend orthogonally from the lateral portions 25 and together provide an aligned sliding fit into the respective grooves and cavities in the jaws 2. Lateral portions of the end effectors and the respective cavities in the jaws also provide lateral support or strength to the jaws 2 preventing misalignment or bending of the jaws. The engagement between the end effectors 4 and the jaws 2 also reduces dislodgement or separation of the components and operatively connects the components together such that movement of end effectors translates to the jaws, providing substantially direct application of force from the handle to the clip, and vice versa, providing tactile feedback to the user.

The jaws 2 being separable from the handle assembly 7 and the cartridge 5 facilitate sterilization of the jaws 2 and/or handle assembly 7. Additionally, the jaws 2 may be disposed without having to replace the handles 8 allowing for new jaws to be provided as desired to minimize costs and to avoid misalignment or jaw deformation. With the jaws 2 also being provided separately from the cartridge 5, the jaws 2 do not have to be disposed with each cartridge change. More than one cartridge 5 may be used during a surgical procedure and thus using the same jaw 2 may reduce costs.

Referring to FIGS. 5A-5B and 6A-6E, the cartridge 5 has a connector or post 31 extending from the cartridge that is releasably engagable with an aperture or receiver 33 in the jaws 2. A corresponding receiver or aperture on the handle assembly 7, in one aspect, is also positioned in alignment with the aperture or receiver in the jaws 2 to also be releasably engagable with the post 31 of the cartridge 5. The post 31 extends in a direction orthogonally from a longitudinal axis of the cartridge from a base or wall of the cartridge 5. The post is deflectable and resilient to snap or flex with projections or cavities along portions of the post, e.g., on its tip, to secure the post to the jaws 2 and/or handle assembly 7. For example, in one aspect, multiple, e.g., four, barbs or generally evenly spaced hemispherical posts with projections provide releasable engagement of the cartridge 5 and the jaws 2 from the handle assembly 7. Gaps or slots between the barbs or post facilitates the flexing of the barbs, which facilitates insertion/removal of the barbs or post into/from the receiver of the jaws 2 and handle assembly 7. The post or barbs provide a releasable engagement or connector of the cartridge 5 to the handle assembly 7, holding the jaws between the cartridge 5 and handle assembly 7. The gaps or slots reduce forces or stress applied to the post or barbs upon insertion/removal.

In one aspect, another similar although smaller connector or post 35 extends from the cartridge 5 near the jaw tips 2a and distal from the finger loops 6 for releasable engagement with an aperture or receiver 37 in one side of the jaws 2. As such, the second post 35 provides additional support and engagement of the cartridge 5 to the jaws 2 and/or handle assembly 7 to hold the cartridge in approximate axial alignment with the handle assembly 7.

The jaws tips 2a have grooves for receiving or grasping a clip. An arm 2b extends from each jaw tip 2a and is configured with a width and thickness sufficient to provide a spring force to return the jaws to a predetermined distance or spacing between the jaws, in harmony with the cantilever spring 12, which is at the same time opening the handles 8. The arms 2b connect or are integrated into an extension plate 2c providing support for the jaw tips 2a and a centering point for the jaws at an axial point of the handles.

Referring now to FIGS. 5A-5F, a cartridge has a slider button or knob 11a to be grasped by a user to manually feed or move a single clip from the cartridge 5 into the jaws 2. Operationally, in one aspect, the slider knob is moved forward towards the jaws 2 to feed one clip into the jaws and retracted to load or prepare another clip for placement into the jaws 2. The knob is coupled to a stud 41 slidably connected to the cartridge in a slot disposed in the cartridge cover. The cartridge cover in one aspect has a vessel stop 45. The stud 41 is connected or integrated with a pusher 47 having an engagement end 47a. The engagement end is configured in one aspect to engage portions of the apex of a clip.

A gang pusher 49 is also provided between the pusher 47 and the rest of the clips to move the remaining clips one place forward as the pusher feeds one or the foremost clip into the jaws 2. The gang pusher 49 may have one or more projections or tabs 49a extending therefrom to assist in moving the clips forward. The gang pusher 49 moves back to an initial position as the knob 11a is moved back or retracted. The tabs of the gang pusher, in one aspect, are resilient or deflectable, e.g., cantilever spring tabs, temporarily moving out of the path of a clip, as the gang pusher is moved back or retracted. In one aspect, the tabs of the gang pusher are rounded facilitating movement of the gang pusher moving back or retracting minimizing interference with the remaining clips in the cartridge.

The gang pusher 49 and the pusher 47 are operationally connected to the stud 41 and thus follow each other's movement. Operationally, in one aspect, the slider knob is moved forward towards the jaws 2 causing the pusher 47 to move one clip from a staging area into a pre-load area in the cartridge near the jaws 2. The stud 41 traverses in a slot in the gang pusher 49 and thus the gang pusher remains stationary.

As the clip reaches the pre-load area, the stud 41 reaches the end of the slot in the gang pusher and contacts a portion of the gang pusher 49. Further movement of the stud towards the jaws moves the pusher 47, which moves the clip from the pre-load area into the jaws 2. The gang pusher 49 moves the remaining clips one place forward such that the forward most dip, i.e., the clip closest to the jaws 2 but not in the jaws, is moved to the staging area in the cartridge. The stud 41 is moved or retracted back to the initial starting position positioning the pusher behind the clip in the staging area and the gang pusher behind the remaining dips.

In one aspect, the clips ride along a clip track or backstop 46. The backstop may be integrated with or attached to the cartridge cover from which the projection 31 extends. In one aspect, the backstop 46 has a plurality of projections or clip tabs 46a, e.g., cantilever spring tabs, to hold clips in position as the gang pusher is retracted and to ensure that only one clip at a time is fed into the jaws 2. In one aspect, the backstop 46 also has a second set of tabs 46b, e.g., cantilever spring tabs, facing in an opposing direction to the clip tabs 46a. The second set of tabs 46b apply tension to assist in securing the backstop 46 to the cartridge 5. For example, the tabs 46b reduce gaps between the components in the cartridge and hold the clips in close planar alignment to prevent the clips from misaligning with the pushers and backstop. The cartridge floor or cover 48 has a groove extending therethrough for engagement with the tabs 46b flexing towards it. As such, the distal most clip or the clip closest to the knob 11a along with the clips to the foremost dip or next dip to be fed into the jaws 2 can move through a series of positions prior to being fed into the jaws 2. Thus, a cartridge and jaws are provided without complex components, springs or timing mechanisms.

In one aspect, the clip track or backstop is removable. As such, the applier can be loaded with another set of clips. For example, a door or opening is provided in an end wall of the cartridge distal from the tissue stop. The backstop extends substantially the entire length of the cartridge and is removed through the door or opening in the cartridge. A tab or projection that becomes visible or accessible after the door in the cartridge is opened or spring biasing the clip track or backstop facilitates removal of the clip track or backstop. A new backstop or a now loaded backstop can be slid back into the cartridge through the door or opening in the cartridge. The tabs of the gang pusher, in one aspect, are resilient or deflectable moving out of the path of the dips, as the clips are loaded into the cartridge with the backstop. In one aspect, the tabs of the gang pusher are rounded facilitating movement of the clips being loaded into the cartridge with the backstop. In one aspect, the backstop with clips are positioned or biased away from the gang pusher until the backstop is fully inserted into the cartridge. Once fully seated within the cartridge, the backstop is biased or otherwise cams towards the gang pusher to hold or enclose the clips between the backstop and the gang pusher. In one aspect, the gang pusher is also removable or provided in at least two portions, one portion for engaging the stud and another having tabs to engage the clips.

In one example operation, the clip applier could be fired exhausting the clips within the cartridge and the cartridge could be replaced with another entire cartridge having a new set of clips. In another example, a portion of the cartridge is replaced, e.g., the backstop removed and then reloaded with clips or another new pre-loaded backstop/clip track is provided. As such, the other components in the cartridge, e.g., the pusher, can be reused and thus minimizing waste and costs.

In FIGS. 7A-7E, a handle assembly 7' with handles 8' and finger loops 6' is secured to a cartridge 5' and jaws 2'. An end effector 4' extends from each end of each handle distal from the finger loops. Each end effector 4', in one aspect, has a projection or post 51 extending generally perpendicularly from the longitudinal axis of the clip applier or a plane generally traversed by the handles 8' during each stroke. In one aspect, the end effectors are in-line or in the same plane as the jaws 2'. The projections 51 or the side surfaces or walls of the end effectors engage the side surfaces or sidewalls of each jaw 2' to provide a substantially direct application of force from the handle to jaws and thus to a clip disposed between the handles 8'. Likewise, a reciprocal force is translated back to the handles 8' and finger loops 6' providing tactile feedback to the user.

The handles 8' are connected to the jaws 2' by a pin or post 52 extending from the pivot point of the handles and the end effectors 4' through a cartridge assembly. A post, barb, support, or swaged bushing 53 also extends from the cartridge 5' through the handles 8' near the finger loops 6'. The support attaches the cartridge and/or jaws to the handles. A similar connection is described in U.S. patent application Ser. No. 10/815,149, filed Mar. 30, 2004, the disclosure of which is hereby incorporated by reference as if set forth herein in full. The handles, in one aspect, have two opposing slots utilized for cartridge/handle stability, support and jaw closure. Extending from the cartridge 5' towards the finger loops 6' is a release tab 54 providing a grasping area to facilitate removal of the cartridge.

In one aspect, the cartridge, jaws, handle assemblies and connections thereto used in various aspects of the present invention may be similar to and/or interchangeable with the cartridges, jaws, handle assemblies and connections thereto described in U.S. patent application Ser. No. 10/381,970, filed Mar. 5, 2004, Ser. No. 10/518,436, filed Dec. 16, 2004, the disclosures of which are hereby incorporated by reference as if set forth in full herein. The cartridge assembly has covers in which the jaws 2' are disposed in between. The cartridge and/or covers have notches or cavities adjacent or proximate to the sidewalls of the jaws where the end effectors engage the jaws. A stabilizer 55 in one aspect is disposed between the jaws 2' to assist in minimizing misalignment of the jaws. In one aspect, a door or opening is provided in the cartridge near the release tab 54. Through the opening, another set of clips can be loaded into the cartridge. For example, a new backstop or a now loaded backstop can be slid back into the cartridge through the door or opening in the cartridge.

Figure 8B:
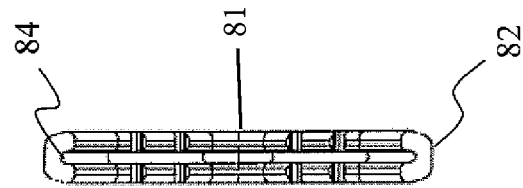
FIG. 8B illustrates a cross-sectional view of one aspect of a surgical clip in accordance with various aspects of the present invention.
Figure 8A:
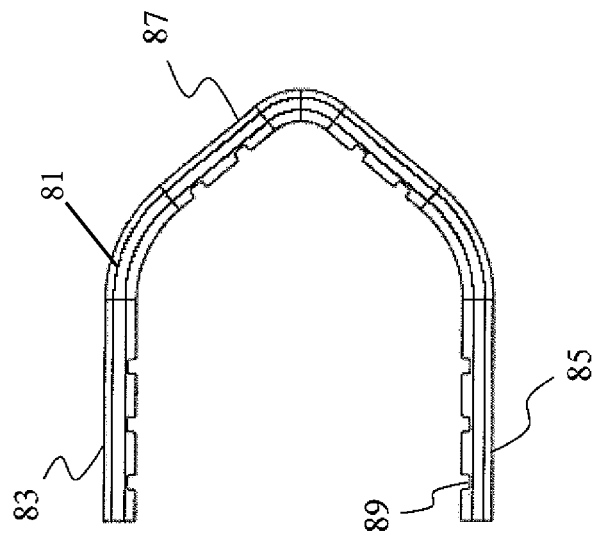
FIG. 8A illustrates a top view of one aspect of a surgical clip in accordance with various aspects of the present invention.
Figure 9A:
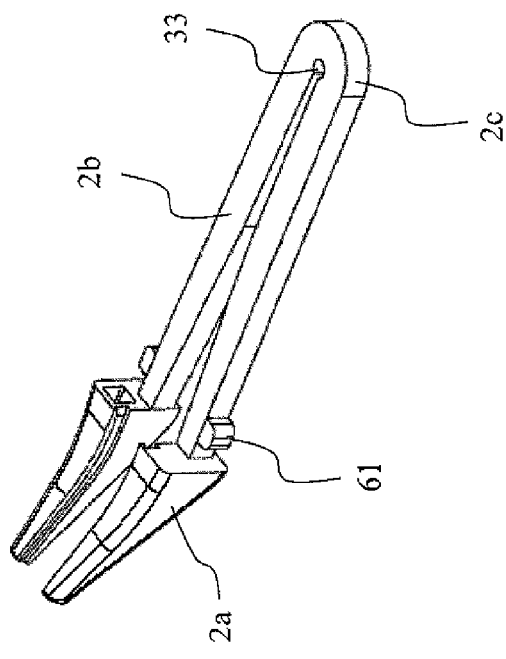
FIG. 9A illustrates a perspective view of one aspect of a jaw in accordance with various aspects of the present invention.
Figure 9B:
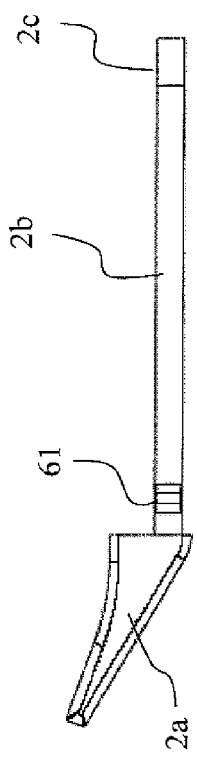
FIG. 9B illustrates a side view of one aspect of a jaw in accordance with various aspects of the present invention.

FIGS. 8-9 illustrate exemplary clips and jaws that may be used in conjunction with various aspects of the present invention. The clip and jaws are sized and shaped as shown to maximized uniform clip closing or deformation while minimizing the force used to close the clip and the over/under closing or crimping of the clip. The clip 81, in one aspect, is generally U-shaped or V-shaped with a pair of outwardly extending and generally opposed legs 83,85 connected at an apex 87. The surface 82 of the clip 81 is substantially flat providing sufficient contact surface area for contacting the engagement end 47a and/or clip track or floor. The clip 81, in one aspect, has grooves or channels 84,89 to facilitate crimping or increase friction and/or occlusion force provided by the clip 81.

In one aspect, the jaws 2 are stabilized by being one piece held in place by the slots and projections to the handles and the grooves in the jaw tips 2a can deflect together for better clip closure due to thin sections in the jaw midsections. The jaws tips 2a have grooves for receiving or grasping a clip. An arm 2b extends from each jaw tip 2a and is configured with a width and thickness sufficient to provide a spring force to return the jaws to a predetermined distance or spacing between the jaws. The arms 2b connect or are integrated into an extension plate or bow 2c providing support for the jaw tips 2a and a centering point for the jaws at an axial point of the handles.

Projections or extensions 61 extend from the jaw arms 2b, in one aspect, providing engagement with the end effectors to close the jaws and/or to connect the cartridge to the jaws. An aperture or receiver 33 in the bow in one aspect releasably connects the cartridge to the handle assembly with the jaws held there between. In one aspect, the jaws and handles used in various aspects of the present invention are reusable and made of metal, e.g., stainless steel. The cartridge, in one aspect, used in various aspects of the present invention is reusable with an autoclavable polymer cover and support.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments and aspects of the present invention should be considered in all respects as illustrative and not restrictive.

The invention claimed is:

1. A surgical clip applier comprising:
   a handle assembly having two movable handles connected at a pivot point;
   wherein each of the two movable handles has a proximal end and distal end, the distal end having an end effector extending therefrom, jaws removably connected to the end effectors of the handle assembly, wherein movement of the proximal ends of the two handles cause the jaws to close or open; and a cartridge carrying multiple surgical clips and having a manually movable actuator attached to the cartridge operationally advancing at least one of the multiple surgical clips within the cartridge such that the manually movable actuator is movable in a first direction to feed one of the multiple surgical clips into the jaws and movable in a second direction opposite the first direction to prepare another one of the multiple surgical clips for placement into the jaws, the manually movable actuator movable independently of the two movable handles, the cartridge removably connected to the handle assembly; wherein the cartridge further comprises:

a pusher connected to the manually movable actuator and slidable to deliver a single clip of the multiple surgical clips to the jaws during a first portion of movement of the manually movable actuator in the first direction; and a gang pusher connected to the pusher, the gang pusher remaining stationary during the first portion of movement of the manually movable actuator and arranged to simultaneously contact and move each clip in the cartridge other than the single clip towards the jaws during a second portion of movement of the manually movable actuator in the first direction.

2. The applier of claim 1 wherein the cartridge is in a first plane and wherein the handle assembly is in a second plane, the second plane being parallel to the first plane and the proximal end of the handle assembly having finger loops.

3. The applier of claim 2 wherein the end effectors have posts removably connected to cavities in the jaws to communicate motion from the finger loops to the jaws.

4. The applier of claim 1 wherein the manually movable actuator comprises a graspable knob slidable relative to the cartridge.

5. The applier of claim 1 wherein the cartridge further comprises means for holding a plurality of clips removably attached to the cartridge.

6. The applier of claim 1 wherein the handle assembly further comprises:
a first and a second handles being connectable to each other through a post and a lock box, each handle having a finger loop extending from a proximal end of each a handle.

7. The applier of claim 6 wherein each handle has a proximal and distal end extending along a longitudinal axis, a planar projection extending parallel to the longitudinal axis of the handle assembly and extending from the distal end of each handle and a first protrusion extending perpendicularly from the planar projection.

8. The applier of claim 7 wherein the jaws have planar slots in parallel to the longitudinal axis of the handle assembly and arranged to receive the planar projection of each handle.

9. The applier of claim 8, wherein each handle further comprises a second protrusion extending perpendicularly from an opposing surface of each handle opposite of a surface from which the first protrusion extends from the planar projection.

10. The applier of claim 1 wherein the cartridge has a proximal end and a distal end with a first connector arranged on the distal end of the cartridge and a second connector arranged on the cartridge between the first connector and the proximal end of the cartridge.

11. The applier of claim 1 wherein the pusher comprises a stud slidably connected to the cartridge.

12. The applier of claim 11 wherein the gang pusher comprises a slot formed therein and wherein the stud is positioned through the slot.

13. The applier of claim 1 wherein gang pusher further comprises a plurality of tabs arranged to simultaneously contact and move each clip in the cartridge towards the jaws.

14. The applier of claim 1 wherein the cartridge further comprises a backstop removably connected to the cartridge and having a plurality of clip tabs spaced along the backstop arranged to simultaneously contact each clip in the cartridge and to restrict movement of each clip away from the jaws.

15. The applier of claim 14 wherein the backstop further comprises a second plurality of tabs extending in an opposite direction to that of the plurality of clip tabs, the second plurality of tabs adapted to secure the backstop to the cartridge.

16. The applier of claim 1, wherein the cartridge has a proximal end and a distal end, and wherein the cartridge comprises a vessel stop at the distal end thereof.

17. A surgical clip applier comprising:
a cartridge carrying multiple surgical clips having a first connector and a second connector, and a longitudinal axis extending from a distal end of the cartridge to a proximal end of the cartridge, each clip being U-shaped with a first leg and a second leg;

a jaw assembly removably coupled to the cartridge, the jaw assembly comprising:

a first jaw having a slot and arranged to receive one of the first and second legs of one clip of the multiple surgical clips, the first jaw having an aperture extending through the first jaw in a direction orthogonal to the longitudinal axis, the first connector operationally connected to the aperture of the first jaw;

a second jaw having a slot and arranged to receive one of the first and second legs of one clip of the multiple surgical clips; and a plate connecting the first and second jaws together and having an aperture through the plate, the second connector operationally connected to the aperture through the plate; and a handle assembly having a receiver positioned therein in alignment with the aperture through the plate such that the second connector holds the jaw assembly between the cartridge and the handle assembly and the handle assembly is removably connected to the second connector of the cartridge and the plate;

wherein the handle assembly further comprises a first handle having a proximal end, a first end effector and a second handle having a proximal end, a second end effector, and wherein the first jaw is removably connected to the first end effector, and the second jaw is removably connected to the second end effector;

wherein the first handle and the second handle are connected at a pivot point, wherein movement of the proximal ends of the two handles cause the jaw assembly to close or open; and wherein the cartridge is removably connected to the handle assembly.

18. The applier of claim 17 wherein the cartridge further comprises:
a slidable pusher arranged to move a single clip a first distance from a staging area in the cartridge to a pre-load area in the cartridge and a second distance to move the single clip into the first and second jaws; and a graspable actuator arranged to move along the longitudinal axis and connected to the slidable pusher.

19. The applier of claim 18 wherein the cartridge further comprises:

a gang pusher connected to the slidable pusher and arranged to move simultaneously with the slidable pusher after the slidable pusher has moved the first distance and to simultaneously contact and move each clip in the cartridge towards the jaws; and a plurality of removable clip tabs spaced along the cartridge arranged to simultaneously contact and prevent movement of each clip in the cartridge away from the jaws.

20. The applier of claim 18, wherein the handle assembly operatively engages the jaw assembly to open and close the jaws independently of motion of the grasper actuator.

\* \* \* \* \*